United States Patent [19]

Otsuka et al.

[11] 4,411,863
[45] Oct. 25, 1983

[54] LOW-CARAT CORROSION-RESISTANT GOLD ALLOY WITH THE SKIN OF THE ALLOY NOT BEING BLACKED UPON CASTING

[76] Inventors: Masasuke Otsuka, 14-8, Okusawa 5-Chome, Setagaya-ku, Tokyo; Hideyo Maniwa, 76, Matsugaoka, Kanagawa-ku, Yokohama-shi, Kanagawa-ken, Tokyo; Shinya Nishina, Naka-so 201, 19-7, Sakura 2-Chome, Setagaya-ku, Tokyo, all of Japan

[21] Appl. No.: 391,941

[22] Filed: Jun. 24, 1982

[30] Foreign Application Priority Data

Jun. 23, 1981 [JP] Japan .............................. 56-95969

[51] Int. Cl.³ ............................................. C22C 5/06
[52] U.S. Cl. .................................... 420/580; 420/505
[58] Field of Search ............................. 420/505, 580

[56] References Cited

U.S. PATENT DOCUMENTS

| | | | |
|---|---|---|---|
| 2,716,605 | 8/1955 | Schatz | 420/580 |
| 3,667,936 | 6/1972 | Katz | 420/580 |
| 3,929,475 | 12/1975 | Ingersoll | 420/505 |

FOREIGN PATENT DOCUMENTS 55-141539  11/1980  Japan .............................. 420/505

*Primary Examiner*—W. Stallard
*Attorney, Agent, or Firm*—Toren, McGeady and Stanger

[57] ABSTRACT

A low-carat corrosion-resistant gold alloy which is not blacked in its skin surface color upon being cast is provided. The alloy is used as cast alloy for reparation of tooth crowns, as general decorative articles, or as contact alloy used in electrical apparatus. The alloy is composed essentially of gold, palladium and silver, with addition thereto of indium in place of copper contained in the conventional alloys, and necessary amounts of zinc or tin as deoxidant. Copper contents have been desired in view of improving the castability and mechanical strength of the alloy but the skin surface of the cast alloy may thereby be blacked to detract from aesthetic effects thus making it necessary to wash off the blacked oxide film by use of strong acid washing agents. The indium added in place of copper affords necessary mechanical properties to the alloy while providing aesthetically desirable silver to gray skin color and making the washing with strong acids unnecessary.

1 Claim, No Drawings

LOW-CARAT CORROSION-RESISTANT GOLD ALLOY WITH THE SKIN OF THE ALLOY NOT BEING BLACKED UPON CASTING

FIELD OF THE INVENTION

This invention relates to low-carat gold alloy used as cast alloy as tooth alloy filling or reparation material, or as alloys used with general ornamental devices or contacts for electrical appliances. It relates more particularly to prevention of blacking of the skin of cast alloy inherent in this kind of low-carat gold alloy and elimination of the procedure for removal of the blacking and the use of drastic washing agents thought to be indispensable for such procedure.

In the following description, reference is made to the dental alloy which is the typical application of the low-carat gold alloy. It is however to be noted that the gold alloy of the present invention is not limited to such application, but may be used extensively for general ornamental articles and electrical contacts as well.

DESCRIPTION OF THE PRIOR ART

Heretofore, low-carat gold alloys for dental application, that is, cast alloys used for reparation of crowns, are composed in known manner of gold, palladium and copper, as shown in Table 1 below, with the gold being contained in an amount of from more than 2 to 35 percent and the palladium being contained in such amount that the combined contents of gold and palladium are essentially equal to 27 to 48 percent.

The copper contents are added for improving the mechanical strength and castability but the addition of copper results in lowered color-fastness and corrosion resistance of the alloy when used in the oral cavity, and coverage of the surface of cast article with black or black to gray oxide films immediately following the casting. When the alloy is used for reparation of tooth crowns, such blackish oxide films are entirely undesirable not only aesthetically but from the viewpoint of mounting or adaptability of the alloy to its base. Therefore, when preparing a crown filling (reparation material), these films must be completely removed from both the inner and outer surfaces of the cast article.

For removal of these blacked oxide films, it is necessary to wash the cast article with strong acids such as hydrochloric acid or sulfuric acid. The use and storage of these washing agents will require special attention and moreover deliberate precautions must be taken in the disposal of washing wastes for avoiding environmental pollution.

By the above reason, corrosion resistant low-carat gold alloy which does not contain copper and which, while satisfying the essential requirements for dental alloys, is highly awsthetic, simple in manufacture and safe in use and which enables facilitated disposal of waste material.

The feature of the inventive alloy resides in its good castability, simplified manufacture steps and clinical properties at least equal to those of conventional alloys notwithstanding complete exclusion of copper contents.

Supposing that, with white low-carat gold alloy containing 2 to 12 percent of gold, more than 10 percent of palladium, more than 40 percent of silver and about 10 percent or more of copper, which is most popular, simply the copper contents have been removed, the resulting alloy may be improved in color fastness, corrosion resistancy and the surface of cast articles. However, the alloy tends to be unusable practically because of lowered castability, workability and mechanical strength.

SUMMARY OF THE INVENTION AND DESCRIPTION OF PREFERRED EMBODIMENTS

The alloy according to the present invention has indium contents in place of copper contents so that the alloy may have improved manouvability (workability) including castability and mechanical properties required of dental alloys, as well as improved corrosion resistancy and fastness of surface color including surface color of cast articles. Among the advantages derived from the present invention, first of all, skin surfaces of the cast articles are silver to gray in color and thus aesthetically satisfactory and thus blacking of the cast surfaces, which has been the deficiency of the conventional low-carat gold alloy, has been eliminated. Moreover, the operations involved after casting may be safe and simple due to elimination of the use of strong acids and the procedure of waste disposal for combatting the pollution may be facilitated. Secondly, physical and other properties required of dental alloys may be met in spite of the absence of copper contents. Thirdly, by the addition of indium, the resulting alloy presents a light white to gray color which is a highly preferred color tint for tooth crown filling. These properties are equally desirable for other applications of the alloy such as ornamental articles in general and contact for electrical apparatuses. It is to be noted that medium to high carat gold alloys free of copper and alloys containing platinum group elements also free of copper are known and used as dental alloys, however, these alloys devoid of copper obviously have no pertinence to the present invention because the effects of copper contents and the range of gold contents are different from those of the inventive alloy.

The present invention will be elucidated further by referring to numerical examples.

TABLE 1

|  | No. 1 | No. 2 | No. 3 | No. 4 |
|---|---|---|---|---|
| gold | 10 | 5 | 3 | 20 |
| palladium | 25 | 30 | 27 | 20 |
| silver | 47 | 55 | 68 | 44 |
| copper | 18 | 10 | 2 | 16 |
| color of cast surface | black | black to gray | gray to black | black |

The above Table 1 shows the typical compositions of the alloys so far known and used, and the surface colors of the castings obtained from these alloys. As apparent from Table 1, the conventional alloys have rather high copper contents and thus the surface color tint, color-fastness and corrosion resistancy of the casting obtained therefrom are rather inferior, although the mechanical properties of the casting are practically sufficient.

TABLE 2

|  | No. 1 | No. 2 | No. 3 |
|---|---|---|---|
| contents |  |  |  |
| gold | 15.0 | 10.4 | 19.7 |
| palladium | 22.0 | 26.7 | 18.3 |
| indium | 15.0 | 17.2 | 8.5 |
| zinc | 4.4 | 1.3 | 6.0 |
| silver | 43.6 | 44.4 | 47.5 |
| hardness (Hμ) | 164 | 169 | 162 |
| tensile strength (Kgf/mm²) | 51 | 45 | 49 |

TABLE 2-continued

|  | No. 1 | No. 2 | No. 3 |
|---|---|---|---|
| elongation (%) | 3.4 | 2.1 | 4.1 |
| color change (JIS)10YR | 9/2 | 8/2 | 9/3 |
| casting surface color | silver | silver to gray | silver |

The above Table 2 refers to examples of the inventive alloy composed of gold and indium with purity in excess of 99.99 percent, palladium with purity in excess of 99.9 percent and zinc with purity provided in JIS-H2107 and -H2141. The respective components were blended according to weight percentage shown in the above Table and fused in a cribtole furnace and graphite crucible into an ingot. The resulting alloy composed of gold, palladium, indium, zinc and silver has a homogeneous ground tissue and is highly stable so that it remains in equilibrium despite small fluctuations in the contents of the respective ingredients.

The compositions and properties of the various examples of the present invention are as shown in FIG. 2, from which it is apparent that the as-cast alloy containing indium in place of copper according to the present invention may be endowed with sufficient technical properties to serve as tooth crown filling material.

The numerical limitation of the various ingredients of the inventive gold alloy has been made by the following reason. First of all, the gold and palladium contents are kept to values only sufficient to assure minimum corrosion resistancy as in the case of copper-containing alloys. The function of the indium which has replaced the copper is to lower the fusing temperature of the silver alloy, to compensate the shortage in the color fastness and corrosion resistancy due to gold and palladium contents and to increase the robustness or strength and hardness of the alloy to withstand the occusive pressure. Zinc has been added in a required amount to serve as deoxidant. Similar effects may be obtained when part or all of the zinc contents are replaced by tin.

The numerical limitation of the respective ingredients has been set within a practically allowable range and especially in view of counterbalancing the various properties required of the dental crown filling alloy, especially its workability, technical properties, tenacity and hardness, on the basis of our conjoint consideration of the changes in the alloy properties caused by the addition of the above alloys and the interaction among the respective elements.

Although the above description has been made of cast dental alloys, it is to be noted that the same applies to the alloys for electrical contacts or ornamental articles as well. It is thus well known that, in the manufacture of these alloys for ornamental articles or electrical contacts, the surface status of the cast articles immediately following casting has marked effects on workability and safety of the articles. Furthermore, it has an important bearing on the anti-pollution measures to be taken and consequently on the economic aspects of the manufacture of the dental alloys. In general, the low-carat gold alloys put to the above usage have copper contents by which the cast skin color of the cast articles may be blacked as in the case of the dental alloys. Thus, strong acids are used similarly as washing agents for the removal of these blacked oxides. In the industrial application of the alloys, the more the amount of the alloys to be manufactured, the more the consumption of the washing agent and hence a greater importance has been attached to coping with the situation.

When put to the above usage, the inventive alloy is expected not only to satisfy the various properties required of ornamental alloy and contact alloy but to greatly simplify or reduce the manufacture process and to facilitate the disposal of waste washing solution with great economical advantages. It has been demonstrated experimentally that the skin of cast articles presents a silver to gray mat color and may be washed rather easily because the cast articles may not be subjected to the formation of surface oxide or present an undesirable black or black to gray color. It may be concluded from these results that the inventive alloy may similarly be used for ornamental articles and electrical contact material.

What is claimed is:

1. A low-carat corrosion-resistant gold alloy, with the skin of the alloy not being blacked upon casting, characterized by the contents of gold in the range from 0.5 to 35 weight percent, palladium in the range from 15 to 35 weight percent, indium in the range from 7 to 18 weight percent, zinc in the range from 0 to 10 weight percent, tin in the range of 0 to 10 weight percent, the balance being silver.

* * * * *